(12) United States Patent
Foster et al.

(10) Patent No.: US 11,583,673 B2
(45) Date of Patent: Feb. 21, 2023

(54) MEDICAL ELECTRICAL LEAD TERMINAL BOOT AND METHOD OF MAKING

(71) Applicant: Cardiac Pacemakers, Inc., St. Paul, MN (US)

(72) Inventors: Arthur J. Foster, Blaine, MN (US); Alex J. Sepulveda, Guaynabo, PR (US); Benjamin J. Haasl, Forest Lake, MN (US); Andrew L. De Kock, Ham Lake, MN (US); James M. English, Tipperary (IE)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 17/023,484

(22) Filed: Sep. 17, 2020

(65) Prior Publication Data
US 2021/0085957 A1    Mar. 25, 2021

Related U.S. Application Data

(60) Provisional application No. 62/903,422, filed on Sep. 20, 2019.

(51) Int. Cl.
*A61N 1/05*    (2006.01)
*A61N 1/375*   (2006.01)
*A61N 1/39*    (2006.01)

(52) U.S. Cl.
CPC ............. *A61N 1/05* (2013.01); *A61N 1/3752* (2013.01); *A61N 1/37512* (2017.08); *A61N 1/39622* (2017.08)

(58) Field of Classification Search
CPC .... A61N 1/05; A61N 1/3752; A61N 1/37512; A61N 1/39622
See application file for complete search history.

(56) References Cited

U.S. PATENT DOCUMENTS

| | | | |
|---|---|---|---|
| 5,366,496 A * | 11/1994 | Dahl | A61N 1/0587 607/119 |
| 5,514,172 A | 5/1996 | Mueller | |
| 5,575,814 A * | 11/1996 | Giele | A61N 1/0573 607/120 |
| 6,183,305 B1 | 2/2001 | Doan et al. | |
| 6,921,295 B2 | 7/2005 | Sommer et al. | |
| 7,641,520 B2 | 1/2010 | Marino | |

(Continued)

OTHER PUBLICATIONS

Jehbco Silicones, Silicone Hardness and Shore Durometer, Jun. 18, 2017, https://jehbco.com.au (Year: 2017).*

(Continued)

*Primary Examiner* — Catherine M Voorhees
(74) *Attorney, Agent, or Firm* — Nelson Mullins Riley & Scarborough LLP (57) ABSTRACT

An implantable medical electrical lead connectable to an electrical header of an implantable medical device includes a lead body extending from a proximal end to a distal end, a lead terminal disposed at the proximal end of the lead body and configured to couple the lead to the electrical header, and a lead boot disposed at the lead terminal. The lead boot includes a strain relief portion and a seal portion. The strain relief portion is formed of a first elastic polymer and the seal portion is formed of a second elastic polymer. The first elastic polymer is different from the second elastic polymer.

13 Claims, 4 Drawing Sheets

(56) References Cited

U.S. PATENT DOCUMENTS

| | | | |
|---|---|---|---|
| 2003/0073348 A1* | 4/2003 | Ries | A61N 1/3752 |
| | | | 439/578 |
| 2004/0049255 A1* | 3/2004 | Jain | A61N 1/056 |
| | | | 607/122 |
| 2004/0064174 A1* | 4/2004 | Belden | H01R 13/187 |
| | | | 607/122 |
| 2008/0009198 A1 | 1/2008 | Marino | |
| 2010/0137928 A1* | 6/2010 | Duncan | A61N 1/05 |
| | | | 439/669 |
| 2010/0179627 A1* | 7/2010 | Floyd | H01R 4/20 |
| | | | 607/116 |
| 2020/0338354 A1* | 10/2020 | Bolea | A61L 31/06 |
| 2021/0085984 A1 | 3/2021 | English et al. | |

OTHER PUBLICATIONS

Lianfeng et al., Improvement of Silicone Rubber Properties by Addition of Nano-SiO2 Particles, Apr. 7, 2016, Journal of Applied Biomaterials & Functional Materials (Year: 2016).*

Everything You Need to Know About Liquid Silicone Rubber, Jun. 17, 2017, Molding, Hot Topics (Year: 2017).*

Jehbco Silicones, How Coefficient of Friction Changes, Jul. 17, 2017, https://jehbco.com.au (Year: 2017).*

Combest, Stacy, NuSil Technology Introduces Fluorosilicone Elastomer for Medical Implants, Feb. 6, 2013, Medical Design & Outsourcing (Year: 2013).*

ISO 5841-3:2013, Implants for Surgery—Cardiac Pacemakers-—Part 3: Low profile connectors (is-1) for implantable pacemakers, (Year: 2013).*

\* cited by examiner

MEDICAL ELECTRICAL LEAD TERMINAL BOOT AND METHOD OF MAKING

CROSS REFERENCE TO RELATED APPLICATION

This application claims priority to Provisional Application No. 62/903,422, filed Sep. 20, 2019, which is herein incorporated by reference in its entirety.

TECHNICAL FIELD

The present disclosure relates to electrical leads for implantable medical devices. More specifically, the disclosure relates to electrical lead terminal boots for an implantable medical electrical lead.

BACKGROUND

Medical devices may be implanted in a subcutaneous pocket to support sensing intrinsic physiological electrical activity, delivering a therapeutic stimulus to patient tissue, or providing other therapy to specific treatment sites. For example, a pulse generator may be implanted in a subcutaneous pocket in a patient's chest, with one or more electrical leads extending from the pulse generator to treatment sites within the patient.

The electrical leads generally include a boot at the lead terminal end where the electrical lead can be electrically and mechanically coupled to the pulse generator. The boot is generally molded in place around the lead terminal or molded as a separate piece and then adhered to the lead terminal. For some electrical leads, such as an IS-1 electrical lead, the boot includes a strain relief portion and a seal portion. The strain relief portion provides mechanical strain relief of the transition from the lead terminal to the flexible lead body when the electrical lead is coupled to the pulse generator. The seal portion isolates the electrical connections between the lead terminal and the pulse generator from the fluids present in the subcutaneous pocket.

The electrical lead can be coupled to the pulse generator by gripping the strain relief portion of the boot and pushing the lead terminal end into a lead port of a header of the pulse generator. Some IS-1 electrical leads require a relatively high insertion force to couple the electrical lead to the pulse generator. Such a high insertion force can make it difficult for a physician to couple the electrical lead to the pulse generator. Other IS-1 leads require a relatively low insertion force making it easier for the physician to couple the electrical lead to the pulse generator. However, such leads may tend to suffer leaks around the seals, resulting in internal electrical shorts causing reduced or no therapy being delivered to the patient as all energy crosses between conductor paths in the header instead of in the body through the lead. Even partial leakage can cause reduced sensing, or increased battery current draw, reducing the product life.

What is needed is a way to provide an electrical lead with a leak-free seal and a low insertion force for ease of use by the physician.

SUMMARY

Example 1 is an implantable medical electrical lead connectable to an electrical header of an implantable medical device. The electrical lead includes a lead body extending from a proximal end to a distal end, a lead terminal disposed at the proximal end of the lead body and configured to couple the lead to the electrical header, and a lead boot disposed at the lead terminal. The lead boot includes a strain relief portion and a seal portion. The strain relief portion is formed of a first elastic polymer and the seal portion is formed of a second elastic polymer. The first elastic polymer is different from the second elastic polymer.

Example 2 is the electrical lead of Example 1, wherein a hardness of the first elastic polymer is greater than a hardness of the second elastic polymer.

Example 3 is the electrical lead of Example 2, wherein the hardness of the first elastic polymer per ASTM D2240 is from 70 A to 80 A and the hardness of the second elastic polymer per ASTM D2240 is from 30 A to 70 A.

Example 4 is the electrical lead of any of Examples 1-3, wherein a coefficient of friction of the second elastic polymer is lower than a coefficient of friction for the first elastic polymer.

Example 5 is the electrical lead of Example 4, wherein the second elastic polymer is a fluorosilicone and the first elastic polymer is a liquid silicone rubber.

Example 6 it the electrical lead of any of Examples 1-5, wherein the strain relief portion includes at least one grip point.

Example 7 is the electrical lead of any of Examples 1-6, wherein the strain relief portion further includes a reinforcement structure disposed along and within the strain relief portion.

Example 8 is the electrical lead of any of Examples 1-7, wherein the strain relief portion further includes a reinforcement structure extending along a portion of an exterior surface of the strain relief portion, the reinforcement structure formed of a third elastic polymer, wherein a hardness of the third elastic polymer is greater than a hardness of the first elastic polymer.

Example 9 it the electrical lead of any of Examples 1-8, wherein the electrical lead is a low-profile IS-1 connector per ISO 5841-3:2013.

Example 10 is a method of making a lead boot for an implantable medical electrical lead connectable to an electrical header of an implantable medical device. The lead boot includes a strain relief portion and a seal portion. The method includes molding the strain relief portion from a first elastic polymer or a polymer precursor to form the first elastic polymer, and molding the seal portion from a second elastic polymer or a polymer precursor to form the second elastic polymer, wherein the second elastic polymer is different from the first elastic polymer.

Example 11 is the method of Example 10, wherein molding the strain relief portion from the first elastic polymer includes injecting the first elastic polymer or the polymer precursor to form the first elastic polymer through a channel of a mold, and molding the seal portion from the second elastic polymer includes injecting the second elastic polymer or the polymer precursor to form the second elastic polymer through another channel of the mold.

Example 12 is the method of Example 10, wherein molding the seal portion from the second elastic polymer includes overmolding the second elastic polymer or polymer precursor to form the second elastic polymer onto the strain relief portion.

Example 13 is the method of Example 10, further including adhering the seal portion to the strain relief portion.

Example 14 is the method of any of Examples 10-13, wherein molding the strain relief portion from the first elastic polymer or the polymer precursor to form the first elastic polymer includes overmolding a reinforcement structure.

Example 15 is the method of any of Examples 10-14, wherein a hardness of the first elastic polymer is greater than a hardness of the second elastic polymer.

Example 16 is an implantable medical electrical lead connectable to an electrical header of an implantable medical device. The electrical lead includes a lead body extending from a proximal end to a distal end, at least one electrode disposed at the distal end of the lead body, a lead terminal disposed at the proximal end of the lead body and configured to couple the lead to the electrical header, and a lead boot disposed at the lead terminal. The lead boot includes a strain relief portion and a seal portion. The strain relief portion is formed of a first elastic polymer and the seal portion is formed of a second elastic polymer. The first elastic polymer is different from the second elastic polymer.

Example 17 is the electrical lead of Example 16, wherein a hardness of the first elastic polymer is greater than a hardness of the second elastic polymer.

Example 18 is the electrical lead Example 17, wherein the hardness of the first elastic polymer per ASTM D2240 is from 70 A to 80 A and the hardness of the second elastic polymer per ASTM D2240 is from 30 A to 70 A.

Example 19 is the electrical lead of Example 17, wherein the hardness of the first elastic polymer per ASTM D2240 is from 60 A to 80 A and the hardness of the second elastic polymer per ASTM D2240 is from 30 A to 60 A.

Example 20 is the electrical lead of any of Examples 16-19, wherein the first elastic polymer and the second elastic polymers are liquid silicone rubbers.

Example 21 is the electrical lead of any of Examples 16-19, wherein the first elastic polymer is a high consistency rubber and the second elastic polymer is a liquid silicone rubber.

Example 22 is the electrical lead of Example 16, wherein a coefficient of friction of the second elastic polymer is lower than a coefficient of friction for the first elastic polymer.

Example 23 is the electrical lead of Example 22, wherein the second elastic polymer is a fluorosilicone and the first elastic polymer is a liquid silicone rubber.

Example 24 is the electrical lead of any of Examples 16-23, wherein the strain relief portion includes at least one grip point.

Example 25 is the electrical lead of any of Examples 16-24, wherein the strain relief portion further includes a reinforcement structure disposed along and within the strain relief portion.

Example 26 is the electrical lead of any of Examples 16-25, wherein the strain relief portion further includes a reinforcement structure extending along a portion of an exterior surface of the strain relief portion, the reinforcement structure formed of a third elastic polymer, wherein a hardness of the third elastic polymer is greater than a hardness of the first elastic polymer.

Example 27 is the electrical lead of any of Examples 16-26, wherein the electrical lead is a low-profile IS-1 connector per ISO 5841-3:2013.

Example 28 is a method of making a lead boot for an implantable medical electrical lead connectable to an electrical header of an implantable medical device. The lead boot includes a strain relief portion and a seal portion. The method includes molding the strain relief portion from a first elastic polymer or a polymer precursor to form the first elastic polymer, and molding the seal portion from a second elastic polymer or a polymer precursor to form the second elastic polymer, wherein the second elastic polymer is different from the first elastic polymer.

Example 29 is the method of Example 28, wherein molding the strain relief portion from the first elastic polymer includes injecting the first elastic polymer or the polymer precursor to form the first elastic polymer through a channel of a mold, and molding the seal portion from the second elastic polymer includes injecting the second elastic polymer or the polymer precursor to form the second elastic polymer through another channel of the mold.

Example 30 is the method of Example 28, wherein molding the seal portion from the second elastic polymer includes overmolding the second elastic polymer or the polymer precursor to form the second elastic polymer onto the strain relief portion.

Example 31 is the method of Example 28, further including adhering the seal portion to the strain relief portion.

Example 32 is the method of Example 28, wherein molding the strain relief portion from the first elastic polymer or the polymer precursor to form the first elastic polymer includes overmolding a reinforcement structure.

Example 33 is the method of any of Examples 28-32, wherein a hardness of the first elastic polymer is greater than a hardness of the second elastic polymer.

Example 34 is an implantable medical electrical lead connectable to an electrical header of an implantable medical device. The electrical lead includes a lead body extending from a proximal end to a distal end, at least one electrode disposed at the distal end of the lead body, a lead terminal disposed at the proximal end of the lead body and configured to couple the lead to the electrical header, and a lead boot disposed at the lead terminal. The lead boot includes a strain relief portion, a seal portion and a reinforcement structure extending along a portion of an exterior surface of the strain relief portion. The reinforcement structure formed of a first elastic polymer and the strain relief portion formed of a second elastic polymer. The first elastic polymer is different from the second elastic polymer.

Example 35 is the electrical lead of Example 34, wherein a hardness of the first elastic polymer is greater than a hardness of the second elastic polymer.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

A more complete understanding is available by reference to the following detailed description of numerous aspects and embodiments of the disclosure. The detailed description which follows is intended to illustrate but not limit the disclosure.

In accordance with various aspects of the disclosure, a medical device is defined as "an implantable medical device" if it is completely or partly introduced, surgically or medically, into the human body or by medical intervention into a natural orifice, and which is intended to remain after the procedure. It is understood that the various embodiments can be implemented in any suitable medical device implanted in a patient that include a housing and an electrical lead electrically connected to the housing, such as the cardiac rhythm management (CRM) system described below. For example, embodiments may be employed with a subcutaneously-implanted implantable cardioverter-defibrillator (ICD) housing and lead system. Other such implantable medical devices include, without limitation, implantable cardiac monitors and neurostimulation systems such as spinal cord stimulation or deep brain stimulation devices.

Figure 1:
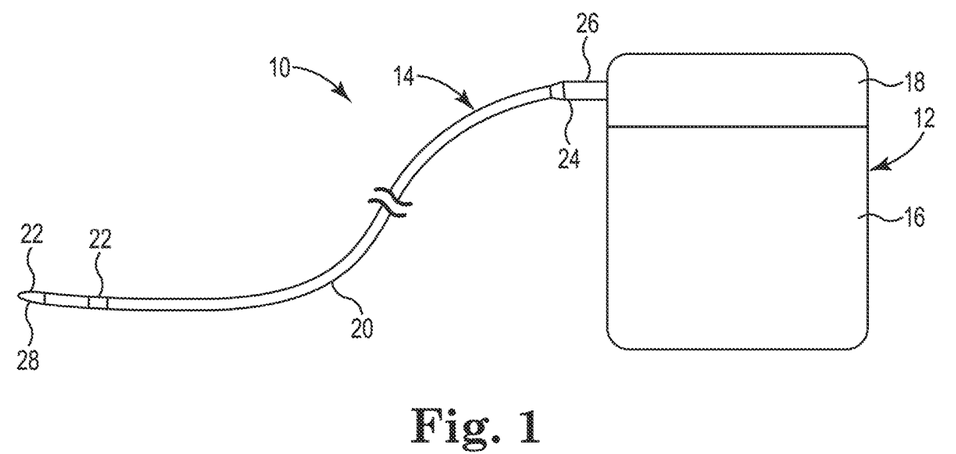
FIG. 1 is a side view of an implantable medical device, according to some embodiments of the disclosure.

FIG. 1 is a side view of an implantable medical device in accordance with some embodiments of the disclosure. FIG. 1 shows a cardiac rhythm management (CRM) system 10 for delivering and/or receiving electrical pulses or signals to stimulate, shock, and/or sense a heart (not shown). The CRM system 10 can include a pulse generator 12 and an electrical lead 14. The pulse generator 12 includes a housing 16 and an electrical header 18 connected to the housing 16. The housing 16 can include a source of power as well as electronic circuitry. The electrical header 18 provides a physical and electrical connection for the electrical lead 14. The connection provided by the electrical header 18 permits the electrical lead 14 to be selectively connected and disconnected to the pulse generator 12. The pulse generator 12 may be a battery-powered device that generates a series of timed electrical discharges or pulses. The pulse generator 12 may be implanted into a subcutaneous pocket made in the wall of the chest. Alternatively, the pulse generator 12 may be placed in a subcutaneous pocket made in the abdomen, or in another location. It should be noted that while the electrical lead 14 is described for use with the heart, the electrical lead 14 is suitable for other forms of electrical stimulation/sensing as well.

The electrical lead 14 can include a lead body 20, at least one electrode 22 (two shown in FIG. 1) and a lead boot 24. The lead body 20 can be flexible, tubular structure formed of a biocompatible polymer, such as silicone or polyurethane, such as polyisobutylene-polyurethane. The electrode 22 can be formed of a biocompatible conductor, such as titanium, stainless steel, iridium, iridium oxide, titanium nitride, platinum, a conductive polymer or combinations of any of these materials, to name a few. The lead boot 24 is described in detail below.

The lead body 20 extends generally from a proximal end 26 to a distal end 28. The at least one electrode 22 can be disposed along a portion of the electrical lead 14, for example near the distal end 28, to electrically couple the electrical lead 14 with the heart. At least one electrical conductor (not shown) may be disposed within the lead body 20 and extend generally from the proximal end 26 to the distal end 28. The at least one electrical conductor electrically connects the electrode 22 with the proximal end 26 of the electrical lead 14 to couple the electrode 22 to the pulse generator 12. So configured, the electrical lead 14 may carry electrical current and pulses between the pulse generator 12 and the heart.

Figure 2:
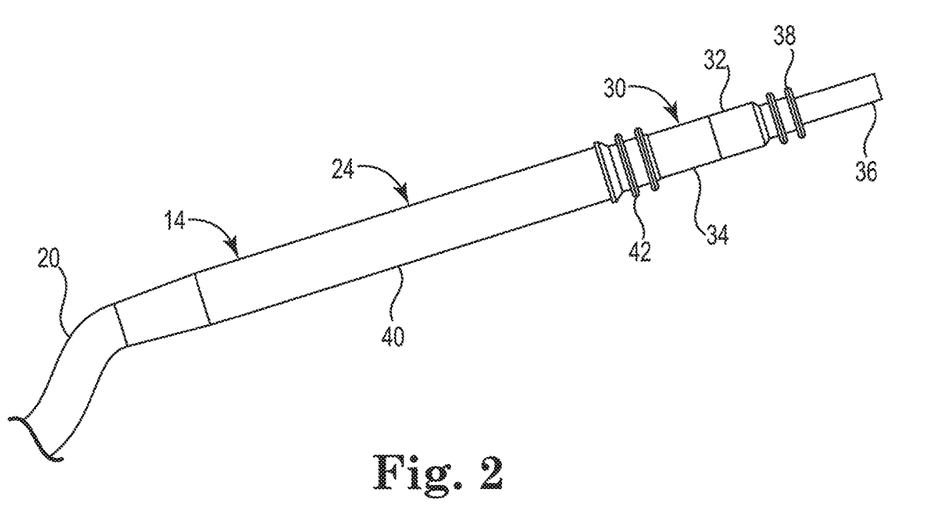
FIG. 2 is a side view of a proximal portion of a medical electrical lead, according to some embodiments of the disclosure.

FIG. 2 is a partial perspective view of a portion of the electrical lead 14, in accordance with some embodiments of the disclosure. FIG. 2 shows a portion of the electrical lead 14 at the proximal end 26 with the electrical lead 14 disconnected from the pulse generator 12. As shown in FIG. 2, the electrical lead 14 further includes a lead terminal 30 disposed at the proximal end 26 of the lead body 20. The lead terminal 30 can include a lead terminal body 32, an electrical contact 34, a terminal pin 36 and a proximal seal 38. The lead terminal body 32 can be a tubular structure formed of a biocompatible non-conductive polymer such as, for example, an aromatic polyether-based thermoplastic polyurethane, polyether ether ketone, a polycarbonate based polyurethane, silicone rubbers, or a hybrid material composed of silicones and polyurethanes. The electrical contact 34 and the terminal pin 36 may be formed of a conductive metal, for example, stainless steel, titanium and its alloys, platinum and its alloys, palladium and its alloys, tantalum and its alloys, and nickel cobalt alloys, such as MP35N. In the embodiment shown in FIG. 2, the electrical contact 34 extends circumferentially around at least a portion of the lead terminal body 32. The terminal pin 36 is disposed at an end of the lead terminal body 32 opposite the lead body 20. Other embodiments may have more than one electrical contact 34 and/or may not have a terminal pin 36. The at least one electrical conductor (not shown) disposed within the lead body 20 may extend through the lead terminal body 32 to the electrical contact 34 and/or to the terminal pin 36 to electrically connect the at least one electrode 22 with the electrical contact 34 and/or terminal pin 36 in lead terminal 30. The proximal seal 38 extends circumferentially around the lead terminal body 32. The proximal seal 38 may be formed of silicones, such as high-consistency rubber (HCR) or liquid silicone rubber (LSR), or polyurethanes, such as polyisobutylene-polyurethane block copolymer or styrene-isobutylene-styrene block copolymer, or any combinations thereof. The proximal seal 38 is configured to seal against an interior surface (not shown) within the electrical header 18 when the electrical lead 14 is coupled to the pulse generator 12 (FIG. 1).

The lead boot 24 includes a strain relief portion 40 and a seal portion 42. The lead boot 24 can physically contact and extend over a portion of the proximal end 26 of the lead body 20 and over a portion of the lead terminal 30. So disposed, the lead boot 24 provides mechanical strain relief of the transition from the lead terminal 30 to the flexible lead body 20 when the electrical lead 14 is connected to the pulse generator 12. The seal portion 42 is distal to the proximal seal 38. The seal portion 42 is configured to seal against an interior surface (not shown) within the electrical header 18 when the electrical lead 14 is coupled to the pulse generator 12 (FIG. 1). In some embodiments, the lead boot 24 and the lead terminal 30 may form a low-profile IS-1 connector per ISO 5841-3:2013, as shown in FIG. 2. In some other embodiments, the lead boot 24 and the lead terminal 30 may form a DF-1 connecter per ISO 11318 or a four-pole connector per ISO 27186:2010, for example.

It has been found that a difficulty in providing an electrical lead with both a leak-free seal and a low insertion force for ease of use by the physician can be due to the use of the same elastic polymer for both a strain relief portion and a seal portion of a lead boot. For example, if a softer elastic polymer is selected for the lead boot to provide a good, compliant seal between the seal portion and the electrical header, the strain relief portion may axially compress when the lead boot and the lead terminal are inserted into the header. The axial compression may cause the strain relief portion to bulge radially outward, causing frictional resistance between the lead boot and the electrical header. The frictional resistance requires a higher insertion force when coupling the electrical lead to the electrical header.

Conversely, if a harder elastic polymer is selected for the lead boot to provide increased axial strength and reduce the axial compression of the strain relief portion, the frictional resistance and the insertion force may be reduced. However, the harder elastic polymer may not provide a good, compliant seal between the seal portion and the electrical header, resulting in leaks.

Figure 3A:
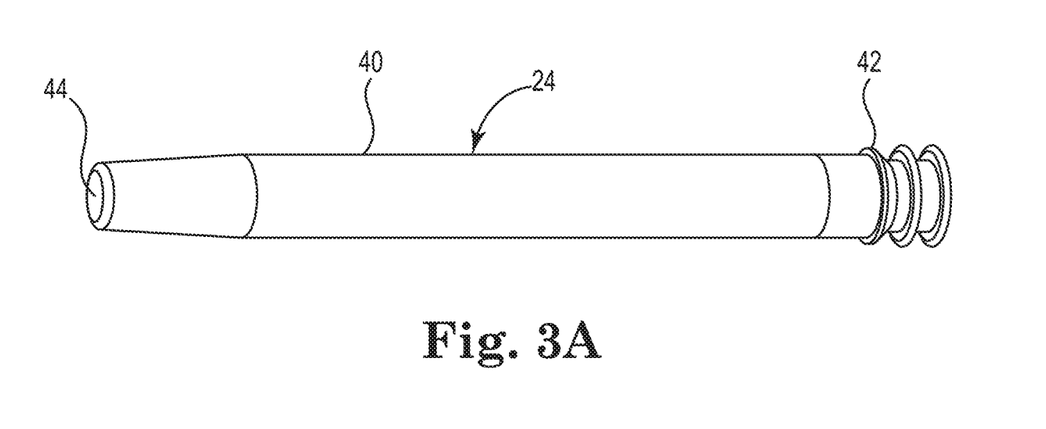
FIGS. 3A and 3B are a perspective side view and an exploded perspective side view of a lead boot, according to some embodiments of the disclosure.
Figure 3B:
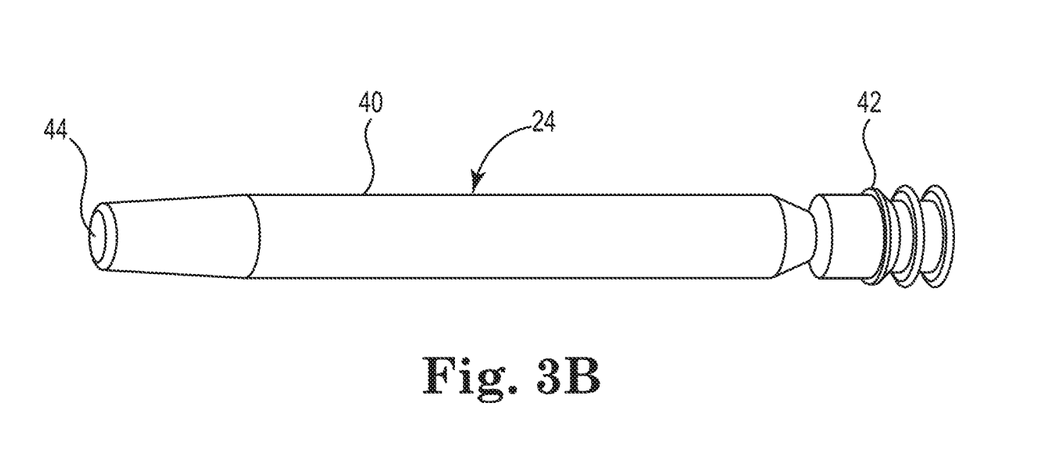

FIGS. 3A and 3B are a perspective side view and an exploded perspective side view of the lead boot 24, according to some embodiments of the disclosure. As shown in FIGS. 3A and 3B, the lead boot 24 further includes a boot lumen 44 formed by the strain relief portion 40 and the seal portion 42, and extending the length of the lead boot 24. A portion of the lead body 20 and the lead terminal 30 are disposed within the boot lumen 44.

The boot lumen 44 may have a diameter as small as 0.17 mm, 0.33 mm, 0.67 mm, 1.0 mm, or 1.3 mm, or as large as 1.7 mm, 2.0 mm, 2.3 mm, 2.7 mm or 3.0 mm, or may be within any range defined between any two of the foregoing values, such as 0.17 mm to 3.0 mm, 0.33 mm to 2.7 mm, 0.67 mm to 2.3 mm, 1.0 mm to 2.0 mm, 1.3 mm to 1.7 mm, or 1.0 mm to 1.7 mm, for example.

In the embodiment shown in FIGS. 3A and 3B, the strain relief portion 40 and the seal portion 42 of the lead boot 24 are formed of two different elastic polymers. As use herein, elastic polymers are different if the differ in at least one of hardness or of coefficient of friction. For example, two liquid silicone rubbers would be considered to be different elastic polymers if they differed in their hardness. It has been found by using two different elastic polymers for the strain relief portion 40 and the seal portion 42 of the lead boot 24, the performance characteristics of each of the strain relief portion 40 and the seal portion 42 can be improved without compromising the performance characteristics of the other portion to provide an electrical lead with both a leak-free seal and a low insertion force.

In some embodiments, the strain relief portion 40 is formed of a first elastic polymer and the seal portion 42 is formed of a second elastic polymer, the hardness of the first elastic polymer is greater than a hardness of the second elastic polymer. The harder first elastic polymer of the strain relief portion 40 can provide the strain relief portion 40 with the axial strength necessary to prevent it from bulging outward and reducing the frictional resistance between the lead boot 24 and the electrical header 18 (FIG. 1). The softer second elastic polymer of the seal portion 42 can provide a good, compliant seal between the seal portion 42 and the electrical header 18 to produce the electrical lead 14 with both a leak-free seal and a low insertion force.

In some embodiments, the first elastic polymer may have a hardness as low as 60 A, 62 A, 64 A, 66 A, 68 A, or 70 A, or as high as 72 A, 74 A, 76 A, 78 A, or 80 A, or may be within any range defined between any two of the foregoing values, such as 60 A to 80 A, 64 A to 78 A, 66 A to 76 A, 68 A to 74 A, 70 A to 72 A, 70 A to 80 A, 72 A to 80 A, or 74 A to 78 A, for example. As used herein, all hardness measurements are per ASTM D2240.

In some embodiments, the second elastic polymer may have a hardness as low as 30 A, 35 A, 40 A, 45 A, or 50 A, or as high as 55 A, 60 A, 65 A, 68 A, or 70 A, or may be within any range defined between any two of the foregoing values, such as 30 A to 70 A, 35 A to 68 A, 40 A to 65 A, 45 A to 60 A, 50 A to 70 A, 55 A to 70 A, 50 A to 65 A, 55 A to 68 A, 30 A to 50 A, 30 A to 60 A, or 60 A to 70 A, for example.

The first polymer may include a thermoset polymer, such as a liquid silicone rubber, high consistency rubber, and castable silicones, for example, or a thermoplastic polymer, such as an of the polyurethanes described above, such as polyisobutylene-polyurethane block copolymer or styrene-isobutylene-styrene block copolymer, for example. The second polymer may include a thermoset polymer, such as a liquid silicone rubber, high consistency rubber, and castable silicones, for example, or a thermoplastic polymer, such as an of the polyurethanes described above, such as polyisobutylene-polyurethane block copolymer or styrene-isobutylene-styrene block copolymer, for example.

Alternatively, or additionally, in some embodiments in which the strain relief portion 40 is formed of a first elastic polymer and the seal portion 42 is formed of a second elastic polymer, a coefficient of friction of the second elastic polymer may be lower than a coefficient of friction of the first elastic polymer. The lower coefficient of friction for the seal portion 42 may reduce the insertion force by reducing the friction between the seal portion 42 and the electrical header 18. A higher coefficient of friction for the strain relief portion 40 may provide for an improved grip for the lead boot 24, making it easier to insert the lead boot 24 and the lead terminal 30 into the electrical header 18.

In such embodiments, the first polymer may include a thermoset polymer, such as a liquid silicone rubber, high consistency rubber, and castable silicones, for example, or a thermoplastic polymer, such as an of the polyurethanes described above, such as polyisobutylene-polyurethane block copolymer or styrene-isobutylene-styrene block copolymer, for example. The second polymer may include a thermoset polymer, such as a fluorosilicone, a liquid silicone rubber, high consistency rubber, and castable silicones, for example, or a thermoplastic polymer, such as an of the polyurethanes described above, such as polyisobutylene-polyurethane block copolymer or styrene-isobutylene-styrene block copolymer, for example.

Figure 4:
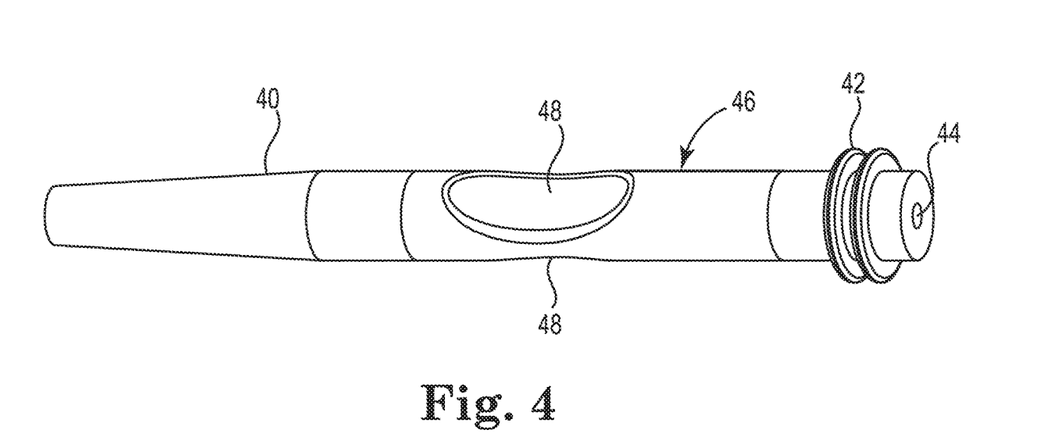
FIG. 4 is a perspective side view of a lead boot, according to some embodiments of the disclosure.

FIG. 4 is a perspective side view of another lead boot, according to some embodiments of the disclosure. FIG. 4 shows a lead boot 46, which can be identical to any of the embodiments of the lead boot 24 described above, except that the strain relief portion 40 includes at least one grip point 48. The embodiment shown in FIG. 4 includes one grip points 48 in the form of two dimples disposed on circumferentially opposite sides of the strain relief portion 40. In the embodiment of FIG. 4, the two grip points 48 are axially aligned. Other embodiments may include more than one grip point 48 disposed along the strain relief portion 40. In some other embodiments, the grip point 48 may be in the form of roughened or ridged regions disposed on circumferentially opposite sides of the strain relief portion 40. The at least one grip point 48 may provide increased friction between the physician's fingers and the lead boot 24 to allow for the application of insertion forces while still maintaining a grip on the lead boot 24.

Figure 5:
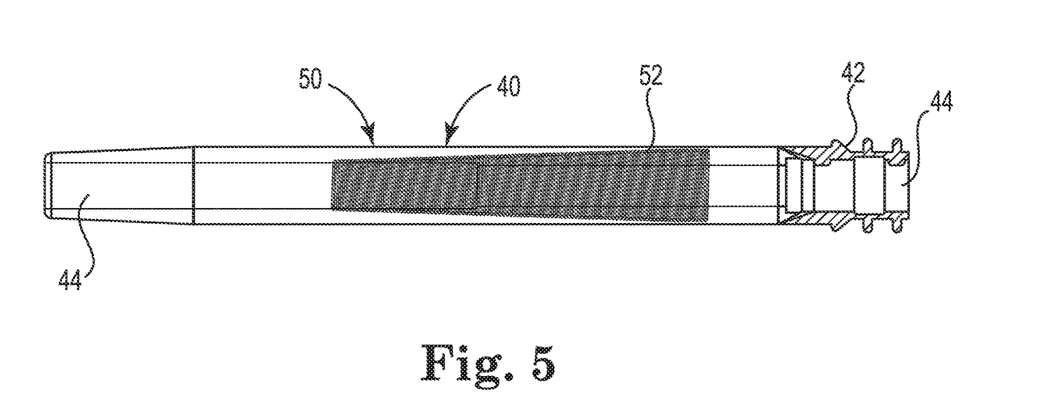
FIG. 5 is a schematic cross-sectional side view of a lead boot including an interior axial reinforcement structure, according to some embodiments of the disclosure.

FIG. 5 is a schematic cross-sectional side view of another lead boot including an interior axial reinforcement structure, according to some embodiments of the disclosure. FIG. 5 shows a lead boot 50, which can be identical to any of the embodiments of the lead boot 24 or the lead boot 46 described above, except that the strain relief portion 40 further includes a reinforcement structure 52. As shown in FIG. 5, the reinforcement structure 52 is disposed along and within the strain relief portion 40. The reinforcement structure 52 is a non-fatigue-inducing component the provides additional axial strength, but permits the strain relief portion 40 to bend, without reducing the fatigue life of the lead boot 50. The reinforcement structure 52 is contained within the lead boot 50. That is, no portion of the reinforcement structure 52 extends beyond the outer surface of the strain relief portion 40 or into the boot lumen 44.

In some embodiments, the reinforcement structure 52 may be a wire coil. The wire of the wire coil may be formed of a metal, such as MP35N®, Elgiloy®, stainless steel, tantalum nitinol, or titanium, for example. The wire of the wire coil may be formed of a polymer, such as polyetheretherketone, a polyurethane, or any combination thereof, for example. The wire of the wire coil may be unifilar or multifilar.

In order to be contained within the lead boot 50 and provide enough additional axial strength, the wire of the wire coil may have a diameter as small as 0.013 mm, 0.02 mm, 0.03 mm, 0.04 mm, or 0.06 mm, or as large as 0.08 mm, 0.10 mm, 0.15 mm, 0.20 mm or 0.25 mm, or may be within any range defined between any two of the foregoing values, such as 0.013 mm to 0.25 mm, 0.02 mm to 0.20 mm, 0.03 mm to 0.15 mm, 0.04 mm to 0.10 mm, or 0.06 mm to 0.08 mm, for example.

In some embodiments, the reinforcement structure 52 may be a bellows, a braid, or a tube including cuts through the tube to permit flexing. The bellows, braid or tube may be formed of metal, such as MP35N®, Elgiloy®, stainless steel, tantalum nitinol, or titanium, for example; a polymer, such as polyetheretherketone, a polyurethane, or any combination thereof; or a polymer-coated metal.

A method of making any of the lead boots described above can include molding the strain relief portion 40 from the first elastic polymer or a polymer precursor to form the first elastic polymer and molding the seal portion 42 from a second elastic polymer or a polymer precursor to form the second elastic polymer. For example, if the first elastic polymer is a thermoplastic polymer, the first elastic polymer may be melted and then injected into a mold for defining the strain relief portion 40. If the first elastic polymer is a thermoset polymer, such as liquid silicone rubber, then a polymer precursor is injected in the mold and permitted to cure to form the first elastic polymer. The polymer precursor may include a pre-polymer and a catalyst mixed together before being injected into the mold. In the same way, if the second elastic polymer is a thermoplastic polymer, the second elastic polymer may be melted and then injected into a mold for defining the seal portion 42. If the second elastic polymer is a thermoset polymer, such as liquid silicone rubber, then a polymer precursor is injected in the mold and permitted to cure to form the second elastic polymer.

In some embodiments, the strain relief portion 40 is molded separately from the seal portion 42, and the process further includes adhering the seal portion 42 to the strain relief portion 40. Adhesives suitable for adhering the seal portion 42 to the strain relief portion 40 may include silicone-based RTV, UV-cured adhesives, cyanoacrylates, for example, or any combination thereof.

In some other embodiments, the strain relief portion 40 and the seal portion 42 may be molded together using a two-sprue mold. The two-sprue mold has two sprues, or channels. One of the channels is connected to a portion of the mold defining the strain relief portion 40 for injecting the first elastic polymer or the polymer precursor to form the first elastic polymer. The other of the channels is connect to a portion of the mold defining the seal portion 42 for injecting the second elastic polymer or the polymer precursor to form the second elastic polymer.

In yet other embodiments, the strain relief portion 40 is molded separately from the seal portion 42, then placed into a mold for defining the seal portion 42, and then the second elastic polymer or a polymer precursor to form the second elastic polymer is injected into the mold to overmold the strain relief portion 40.

The method for making the lead boot 50, which includes the reinforcement structure 52, further includes placing the reinforcement structure 52 in the mold for defining the strain relief portion 40, and then overmolding the reinforcement structure 52 when molding the strain relief portion 40.

Figure 6A:
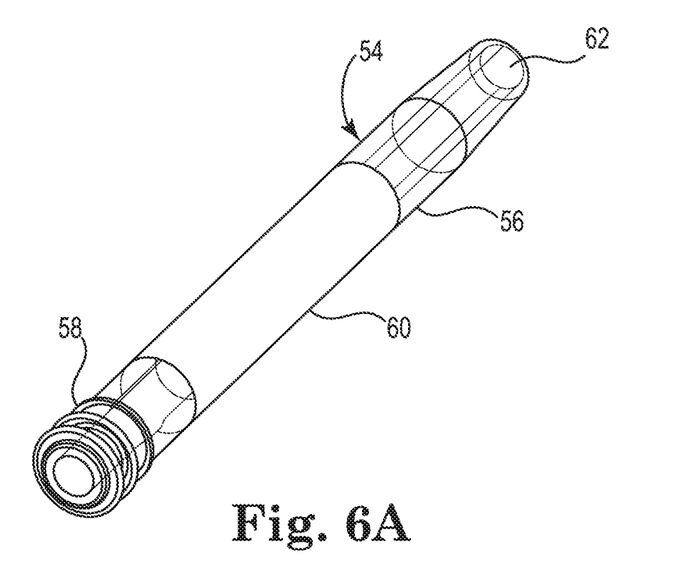
FIGS. 6A and 6B are schematic perspective side views of another lead boot, according to some other embodiments of the disclosure.

FIGS. 6A and 6B are schematic perspective side views of a lead boot 54, according to some other embodiments of the disclosure. As shown in FIG. 6A, the lead boot 54 is an alternative to the lead boot 24 in the CRM system 10 and the electrical lead 14 as described above in reference to FIGS. 1 and 2. The lead boot 54 includes a strain relief portion 56, a seal portion 58, and a reinforcement structure 60. The strain relief portion 56 and the seal portion 58 form a boot lumen 62. The boot lumen 62 may be as describe above for the boot lumen 44 in reference to FIGS. 3A and 3B. The reinforcement structure 60 extends along an exterior surface of the strain relief portion 56. In some embodiments, the reinforcement structure 60 has a tubular shape that extends around the circumference of the strain relief portion 56.

Figure 6B:
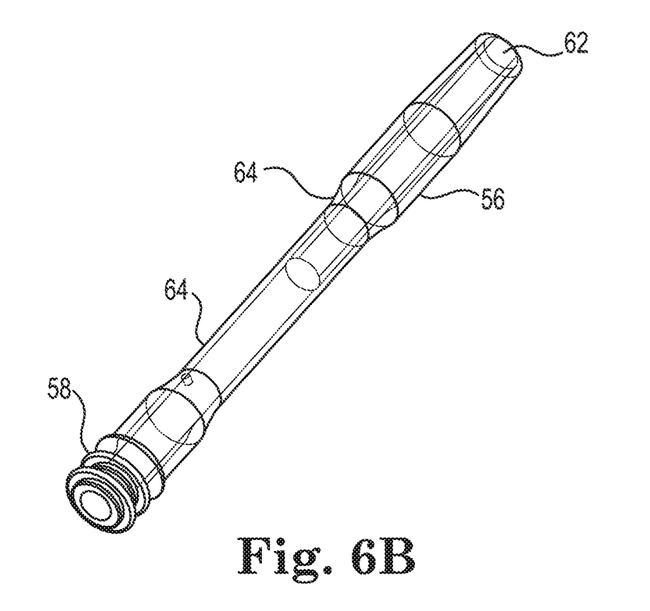

FIG. 6B shows the lead boot 54 without the reinforcement structure 60. As shown in FIG. 6B, in some embodiments, the strain relief portion 56 can form a recessed region 64 extending along the exterior surface of the strain relief portion 56 corresponding to the extent of the reinforcement structure 60. The recessed region 64 can provide space for the reinforcement structure 60 so that the lead boot 54 has a constant diameter along the strain relief portion 56. As with the reinforcement structure 52 described above in reference to FIG. 5, the reinforcement structure 60 is a non-fatigue-inducing component the provides additional axial strength, but permits the strain relief portion 56 to bend, without reducing the fatigue life of the lead boot 54.

In some embodiments, the strain relief portion 56 and the seal portion 58 may be formed of different elastic polymers, as described above for the strain relief portion 40 and the seal portion 42. The reinforcement structure 60 can be formed of a third elastic polymer, which is harder than first elastic polymer used for the strain relief portion 56. The reinforcement structure 60 can provide the strain relief portion 56 with additional axial strength as necessary to prevent it from bulging outward and increasing the frictional resistance between the lead boot 54 and the electrical header 18.

In some other embodiments, the strain relief portion 56 and the seal portion 58 may be formed of the same elastic polymer. In such embodiments, the elastic polymer can be a softer elastic polymer, such as the second elastic polymer described above for the seal portion 42, to provide for a leak-free seal. The reinforcement structure 60 can be formed of the first elastic polymer described above for the strain relief portion 40, which is harder than second elastic polymer. The reinforcement structure 60 can provide the strain relief portion 56 with the axial strength necessary to prevent it from bulging outward and increasing the frictional resistance between the lead boot 54 and the electrical header 18 (FIG. 1). The softer second elastic polymer of the seal portion 58 can provide a good, compliant seal between the seal portion 58 and the electrical header 18 to produce the electrical lead 14 with both a leak-free seal and a low insertion force. The lead boot 54 may be made by any of the methods described above.

As used herein, the phrase "within any range defined between any two of the foregoing values" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. An implantable medical electrical lead connectable to an electrical header of an implantable medical device, the electrical lead comprising:
    a lead body extending from a proximal end to a distal end;
    at least one electrode disposed at the distal end of the lead body;
    a lead terminal disposed at the proximal end of the lead body and configured to couple the lead to the electrical header; and
    a lead boot disposed at the lead terminal, the lead boot defining a boot lumen, the proximal end of the lead body received within the boot lumen, the lead boot including a strain relief portion and a seal portion, the strain relief portion formed of a first elastic polymer and the seal portion formed of a second elastic polymer, wherein the first elastic polymer is different from the second elastic polymer, and wherein the strain relief portion further includes a reinforcement structure disposed along and contained within the strain relief portion such that no portion of the reinforcement structure extends beyond an outer surface of the strain relief portion or into the boot lumen.

2. The electrical lead of claim 1, wherein a hardness of the first elastic polymer is greater than a hardness of the second elastic polymer.

3. The electrical lead of claim 2, wherein the hardness of the first elastic polymer per ASTM D2240 is from 70 A to 80 A and the hardness of the second elastic polymer per ASTM D2240 is from 30 A to 70 A.

4. The electrical lead of claim 2, wherein the hardness of the first elastic polymer per ASTM D2240 is from 60 A to 80 A and the hardness of the second elastic polymer per ASTM D2240 is from 30 A to 60 A.

5. The electrical lead of claim 1, wherein the first elastic polymer and the second elastic polymers are liquid silicone rubbers.

6. The electrical lead of claim 1, wherein the first elastic polymer is a high consistency rubber and the second elastic polymer is a liquid silicone rubber.

7. The electrical lead of claim 1, wherein a coefficient of friction of the second elastic polymer is lower than a coefficient of friction for the first elastic polymer.

8. The electrical lead of claim 7, wherein the second elastic polymer is a fluorosilicone and the first elastic polymer is a liquid silicone rubber.

9. The electrical lead of claim 1, wherein the strain relief portion includes at least one grip point.

10. The electrical lead of claim 1, wherein the reinforcement structure is formed of a third elastic polymer, wherein a hardness of the third elastic polymer is greater than a hardness of the first elastic polymer.

11. The electrical lead of claim 1, wherein the electrical lead is an IS-1 connector per ISO 5841-3:2013.

12. An implantable medical electrical lead connectable to an electrical header of an implantable medical device, the electrical lead comprising:
    a lead body extending from a proximal end to a distal end;
    at least one electrode disposed at the distal end of the lead body;
    a lead terminal disposed at the proximal end of the lead body and configured to couple the lead to the electrical header; and
    a lead boot disposed at the lead terminal, the lead boot including a strain relief portion, a seal portion and a reinforcement structure extending over and along a recessed portion of the strain relief portion, the reinforcement structure formed of a first elastic polymer and the strain relief portion formed of a second elastic polymer, wherein the first elastic polymer is different from the second elastic polymer.

13. The electrical lead of claim 12, wherein a hardness of the first elastic polymer is greater than a hardness of the second elastic polymer.

* * * * *